(12) United States Patent
Steckner et al.

(10) Patent No.: US 10,342,558 B2
(45) Date of Patent: Jul. 9, 2019

(54) TARGET TRACKING METHOD AND APPARATUS FOR RADIATION TREATMENT PLANNING AND DELIVERY

(75) Inventors: Michael C. Steckner, Richmond Heights, OH (US); Peter Boernert, Hamburg (DE); Kay Nehrke, Ammersbek (DE)

(73) Assignee: Koninklijke Philips N.V., Eindhoven (NL)

( * ) Notice: Subject to any disclaimer, the term of this patent is extended or adjusted under 35 U.S.C. 154(b) by 2896 days.

(21) Appl. No.: 10/573,727

(22) PCT Filed: Sep. 10, 2004

(86) PCT No.: PCT/IB2004/051741
§ 371 (c)(1),
(2), (4) Date: Mar. 7, 2007

(87) PCT Pub. No.: WO2005/030330
PCT Pub. Date: Apr. 7, 2005

(65) Prior Publication Data
US 2007/0244386 A1    Oct. 18, 2007

Related U.S. Application Data

(60) Provisional application No. 60/507,634, filed on Sep. 30, 2003.

(51) Int. Cl.
*A61B 5/11* (2006.01)
*A61N 5/10* (2006.01)
(Continued)

(52) U.S. Cl.
CPC .......... *A61B 17/2256* (2013.01); *A61B 34/20* (2016.02); *A61B 90/36* (2016.02);
(Continued)

(58) Field of Classification Search
CPC ................... A61B 5/055; A61B 2019/5236
(Continued)

(56) References Cited

U.S. PATENT DOCUMENTS 6,067,465 A * 5/2000 Foo et al. ............... 600/410
6,144,875 A   11/2000 Schweikard
(Continued)

FOREIGN PATENT DOCUMENTS

EP    1 319 368 A2    6/2003
JP    6315541 A       11/1994
(Continued)

OTHER PUBLICATIONS

Manke, D., et al.; Novel Prospective Respiratory Motion Correction Approach for Free-Breathing Coronary MR Angiography; 2003; MRM; 50:122-131.
(Continued)

*Primary Examiner* — Hien N Nguyen (57) ABSTRACT

A target treatment apparatus for treating a target region (130) within a subject (140) is provided. The apparatus includes an MRI apparatus (100) for generating MR images during an MR scan of the subject disposed within an examination region (110). The apparatus further includes an MRI localizer (150) for receiving the image data from the MRI apparatus wherein the target (130) is localized and a reference marker localizer (160, 160') for non-invasively receiving reference data from a plurality of reference points disposed in proximity to the target wherein the reference points are localized. A tracking processor (300) is also included in the apparatus for receiving localized data from the MRI localizer wherein a relationship between the reference markers and the target region is generated.

14 Claims, 6 Drawing Sheets

(51) Int. Cl.
*A61N 7/02* (2006.01)
*A61B 17/00* (2006.01)
*A61B 34/10* (2016.01)
*A61B 34/20* (2016.01)
*A61B 5/055* (2006.01)
*A61B 90/00* (2016.01)
*A61B 17/225* (2006.01)

(52) U.S. Cl.
CPC ............. *A61N 5/1049* (2013.01); *A61N 7/02* (2013.01); *A61B 5/055* (2013.01); *A61B 5/1127* (2013.01); *A61B 2017/00699* (2013.01); *A61B 2034/105* (2016.02); *A61B 2034/2051* (2016.02); *A61B 2034/2055* (2016.02); *A61B 2034/2072* (2016.02); *A61B 2090/374* (2016.02); *A61B 2090/3937* (2016.02); *A61B 2090/3995* (2016.02); *A61N 5/1037* (2013.01); *A61N 5/1067* (2013.01); *A61N 2005/1055* (2013.01)

(58) Field of Classification Search
USPC ......................................................... 600/411
See application file for complete search history.

(56) References Cited

U.S. PATENT DOCUMENTS

| 6,219,403 | B1 | 4/2001 | Nishihara | |
| 6,289,233 | B1* | 9/2001 | Dumoulin et al. | 600/410 |
| 6,374,132 | B1* | 4/2002 | Acker et al. | 600/411 |
| 6,405,072 | B1 | 6/2002 | Cosman | 600/426 |
| 6,501,981 | B1* | 12/2002 | Schweikard et al. | 600/427 |
| 6,516,211 | B1 | 2/2003 | Acker et al. | 600/411 |
| 6,535,574 | B1 | 3/2003 | Collins et al. | 378/65 |
| 6,708,054 | B2 | 3/2004 | Shukla et al. | 600/411 |
| 2002/0026115 | A1 | 2/2002 | Nehrke et al. | 600/410 |
| 2002/0091314 | A1 | 7/2002 | Schlossbauer et al. | 600/407 |
| 2002/0115923 | A1 | 8/2002 | Erbel | 600/407 |
| 2002/0193681 | A1* | 12/2002 | Vitek et al. | 600/411 |
| 2004/0092815 | A1* | 5/2004 | Schweikard et al. | 600/425 |
| 2004/0267111 | A1 | 12/2004 | Feinberg | 600/411 |

FOREIGN PATENT DOCUMENTS

| JP | 11009708 A | 1/1999 |
| JP | 11197259 A | 7/1999 |
| JP | 2002200182 A | 7/2002 |
| WO | 0241776 A1 | 5/2002 |
| WO | 2005030330 A1 | 4/2005 |

OTHER PUBLICATIONS

Salomir, R., et al.; Local Hyperthermia with MR-Guided Focused Ultrasound: Spiral Trajectory of the Focal Point Optimized; 2000; J. Mag. Res. Imag.; 12:571-583.

* cited by examiner

TARGET TRACKING METHOD AND APPARATUS FOR RADIATION TREATMENT PLANNING AND DELIVERY

CROSS REFERENCE TO RELATED APPLICATIONS

This application claims the benefit of U.S. provisional application Ser. No. 60/507,634 filed Sep. 30, 2003, which is incorporated herein by reference.

The present invention relates to the medical imaging arts. It finds particular application in conjunction with medical imaging in MRI scanners for oncological applications and will be described with particular reference thereto. It will be appreciated, however, that the invention is also applicable to other types of interventional procedures and for other imaging for other purposes.

In planning an interventional procedure, an oncologist typically generates a plurality of images, such as x-ray projection images, of a region to be treated. The images show bone and other internal structures, but do not necessarily differentiate the tumor from non-cancerous tissue. However, from a priori knowledge of anatomy and the nature of the tumor, the oncologist estimates the center of the tumor and its extent.

One of the factors in planning oncological procedures is accurately aligning an interventional tool with the internal tumor. In one case, the interventional tool is a linear accelerator (linac) which emits a high energy x-ray beam for use in radiation therapy. Another interventional tool is a focused ultrasound which emits a high power ultrasonic beam that is used to heat abnormal tissue to the point that it is destroyed, or ablated. In either case, the oncologist aligns the tool with the internal tumor. If the selected trajectory is even slightly off, the x-ray or ultrasonic beam might treat most of the tumor, but may leave a portion of the tumor untreated and may undesirably affect otherwise healthy tissue.

Accordingly, the oncologist typically determines a plurality of trajectories through the tumor which miss neighboring tissue or attenuating bone. Once the trajectories and points of entry into the subject have been determined, the oncologist positions the tool to aim its beam to enter the subject at the selected point of entry and follow a selected trajectory.

The more precisely the size, shape, and position of the tumor are known, the more precisely the treatment beam can be shaped to minimize the exposure of surrounding tissue while assuring the treatment of all cancerous tissue. However, because the oncologist is estimating the extent and location of the tumor without precise visual confirmation, the treatment beam is typically wider than necessary to assure all cancerous tissue is affected. In the case of the linac, the x-ray beam is collimated to have a diameter slightly larger than the tumor to be irradiated. Making the diameter of the beam too large may undesirably irradiate otherwise healthy tissue, however. On the other hand, making the beam diameter smaller increases a probability that cancerous tissue misses being irradiated. The same is analogously true for focused ultrasound.

Tumor motion, along with size and location of the tumor, can also be a factor in planning oncological procedures when it comes to accurately aligning an interventional tool with an internal tumor. For example, a tumor may move due to respiratory motion during treatment. Here, clinical practice has been to identify the tumor then add a margin around the tumor that accounts for tumor motion. The larger the degree of motion, the larger the margin is made in an attempt to ensure that during treatment the entire tumor is irradiated. As discussed above, a consequence of this added margin can be that healthy tissue can be adversely exposed to treatment.

Gating the intervention with respect to such motion has been used in an effort to reduce the margin size and thus reduce the amount of healthy tissue that is otherwise exposed to treatment. In the case of radiation and ultrasound therapy, the delivery of treatment is gated, or selectively turned on or off in response to a gating trigger.

Typical gating triggers, in cases in which respiratory motion is an issue, include bellows to measure the expansion of the chest, breathing sensors which indicate stages of the breathing cycle, or a fiducial marker placed on the subject. Here, the treatment beam is shut off during stages outside the desired portion of the breathing cycle. Unfortunately, gating prolongs the time required for each treatment session since the treatment is not delivered continuously. Another drawback to these gating technologies is that they are largely one dimensional and correlation between tumor position and a 1D measurement is not particularly strong.

Tumor tracking has also been used in an effort to reduce the margin size associated with tumor treatment procedures. Here, to track the movement of the target, one or more internal markers have been attached to or placed near various locations on or near the target organ. Then, as the target moves, the internal markers also move. From the placement of the internal markers, it is possible to determine the position of the target using imaging techniques such as x-ray or ultrasound.

A drawback to this method of tumor tracking, however, is that it involves the invasive procedure of implanting the internal markers. In addition, the internal markers can migrate over time, thereby producing misleading information.

Those skilled in the art will, upon reading and understanding the appended description, appreciate that aspects of the present invention address the above and other matters.

In accordance with one aspect of the invention, a target treatment apparatus for treating a target region within a subject is provided. The apparatus includes an MRI apparatus for generating MR images during an MR scan of the subject disposed within an examination region, an MRI localizer for receiving the image data from the MRI apparatus wherein the target is localized, a reference marker localizer for non-invasively receiving reference data from a plurality of reference points disposed in proximity to the target wherein the reference points are localized, and a tracking processor for receiving localized data from the MRI localizer wherein a relationship between the reference markers and the target region is generated.

In accordance with another aspect of the invention a method of treating a target region within a subject is provided. The method includes generating magnetic resonance images of the subject disposed within an examination region, localizing the target region from the MR images, non-invasively localizing a plurality of reference points disposed in proximity to the target, and generating a relationship between the reference markers and the target region.

In accordance with another aspect of the invention, an apparatus for treating a target region within a subject is provided. The apparatus includes means for generating magnetic resonance images of the subject disposed within an examination region, localizing means for localizing the target region from the MR images, reference means for non-invasively localizing a plurality of reference points disposed in proximity to the target, and modeling means for generating a relationship between the reference markers and the target region.

One advantage of an embodiment of the invention is that a need for directly tracking a target tissue is reduced.

Another advantage of an embodiment of the invention is that restriction of subject movement is reduced.

Another advantage of an embodiment of the invention is that it facilitates target position predictive accuracy.

Another advantage of an embodiment of the invention is that it facilitates the reduction of treatment margins.

Another advantage of an embodiment of the invention is that it facilitates a reduction in radiation doses in treatment sessions.

Another advantage of an embodiment of the invention is that it facilitates a reduction in duration of treatment sessions.

Another advantage of an embodiment of the invention is that it facilitates locating internal subject structures during treatment sessions.

Another advantage of the present invention is that it is non-invasive.

Still further advantages of the present invention will become apparent to those of ordinary skill in the art upon a reading and understanding of the following description of the preferred embodiments.

The invention may take form in various components and arrangements of components, and in various steps and arrangements of steps. The drawings are only for purposes of illustrating a preferred embodiment and are not to be construed as limiting the invention.

Figure 1:
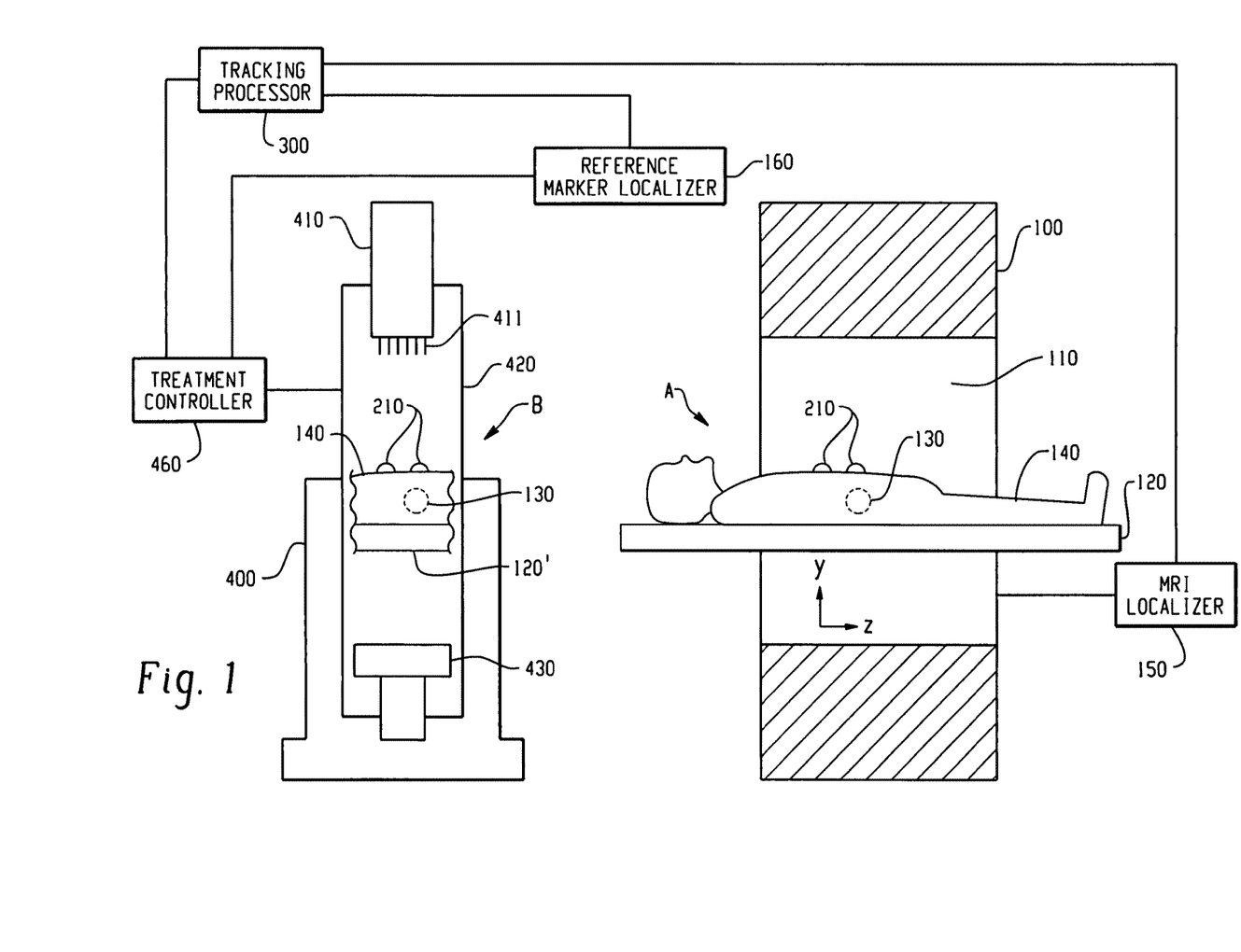
FIG. 1 is an illustration of a target treating apparatus.

With reference to FIG. 1, a target treating apparatus is shown. As shown, the apparatus may serve as an oncological apparatus for the treatment of cancerous tissue, or tumors. The apparatus includes a magnetic resonance imaging (MRI) system 100. The MRI system in the illustrated embodiment is a cylindrical-type system. More specific to the embodiment shown, the MRI system is a horizontal field MRI system which generates a horizontal magnetic field through an imaging region 110 along the axis of its bore. A subject support 120 is movable in to and out of the bore to position a region of interest 130 of a subject 140 in the imaging region 110 as indicated by position A in FIG. 1. In the embodiment shown, external reference, or fiducial, markers 210 are placed on the subject such that they are positioned within the imaging region 110 and in a desired proximity to the region of interest 130. In the embodiment shown, the fiducial markers are compatible with the magnetic fields associated with magnetic resonance imaging and optionally are selected so as to appear on images generated by the MRI apparatus. With respect to the MRI apparatus 100, alternately, an open field MRI system can be used.

Figure 2:
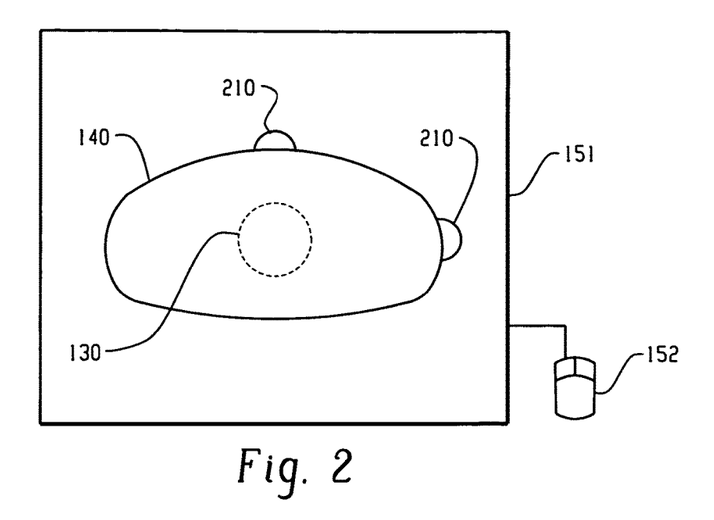
FIG. 2 is an illustration of an MRI localizer showing an axial view of a subject.

The apparatus also includes an MRI localizer 150 for processing images generated by the MRI system. The localizer localizes the region of interest 130, such as an internal tumor, and optionally the reference markers 210. As shown in FIG. 2, the MRI localizer may include such items as a human readable display 151, a pointing device 152, such as a computer mouse or trackball, a keyboard (not shown), and other image processing tools as are known in the relevant art.

In the embodiment shown in FIG. 2, an axial cross section of the subject 140 is shown on the display 151. The cross-sectional image shows the tumor 130 and, optionally, the fiducial markers 210.

Figure 3:
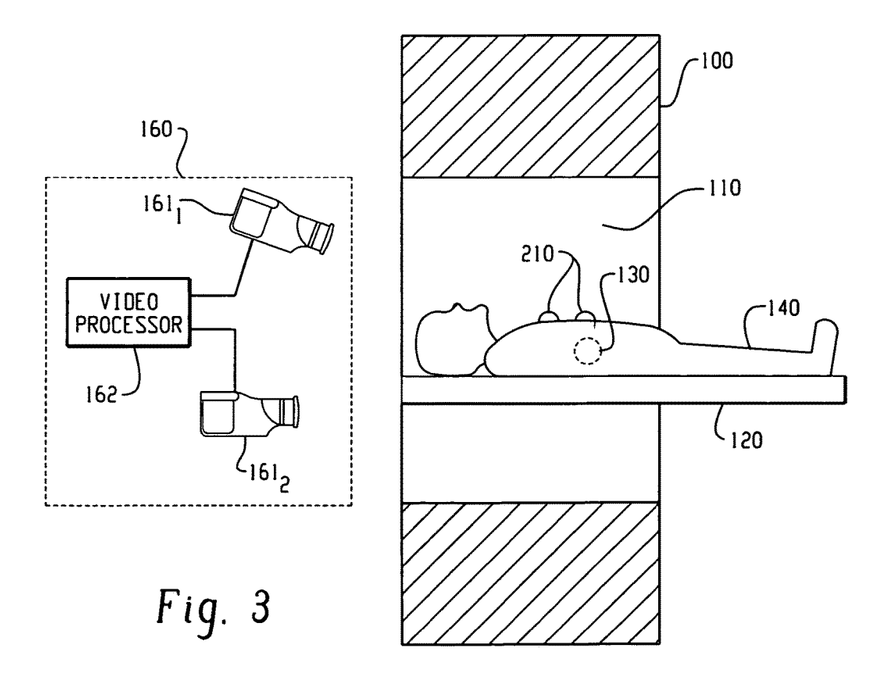
FIG. 3 is an illustration of a reference marker localizer.

Turning back to FIG. 1, the treatment apparatus also includes a reference marker localizer 160 for localizing the reference marker positions. In one embodiment, as shown in FIG. 3, the reference marker localizer includes two video cameras $161_1$, $161_2$ positioned to capture video images of the reference markers 210 from with the examination region 110. Here, the markers can be light reflective. Alternately the markers can emit a light signal an infrared signal, or other signal that can be detected by the video cameras. It is to be understood that while FIG. 3 shown two video cameras, an alternate number of cameras may be chosen so long as the positions of the markers 210 can be determined in three dimensions.

Continuing with FIG. 3, the reference marker localizer 160 also includes a video processor 162. The video processor 162 is connected to the video cameras and includes processors and controls for processing images received therefrom and for identifying the reference markers 210 from the images, as is known in the art. It is also to be understood that other types of position sensing systems, such as audio signal detector with audio signal emitting markers, are contemplated.

Returning to FIG. 1, the MRI localizer 150 and the reference marker localizer 160 pass data regarding the localization of the tumor 130 and the reference markers 210, respectively, to a tracking processor 300. The tracking processor includes a processor that generates a model relating the position of the tumor with respect to the external markers.

The tracking processor is also connected to a treatment controller 460 for transferring the model information thereto. The treatment controller is connected to a treatment tool 400 for controlling a treatment of the subject as more fully described below.

Continuing with FIG. 1, the treatment may be carried out when the subject is within a treatment region of the interventional tool 400, as indicated by position B in FIG. 1. (For the sake of simplicity, a section the subject is shown in position B.) In the embodiment shown, the interventional tool includes a linear accelerator 410, a supporting C-arm 420, and an X-ray detector 430.

In the embodiment shown, the reference marker localizer 160 is used to receive information regarding the external reference markers 210 and processes such data to generate reference marker localization data from position B. This localization data is passed to the treatment controller 460. The treatment controller 460 uses the model information in conjunction with the position B reference localization data to control the treatment tool 400 in accordance with a desired treatment of the tumor 130.

Figure 4A:
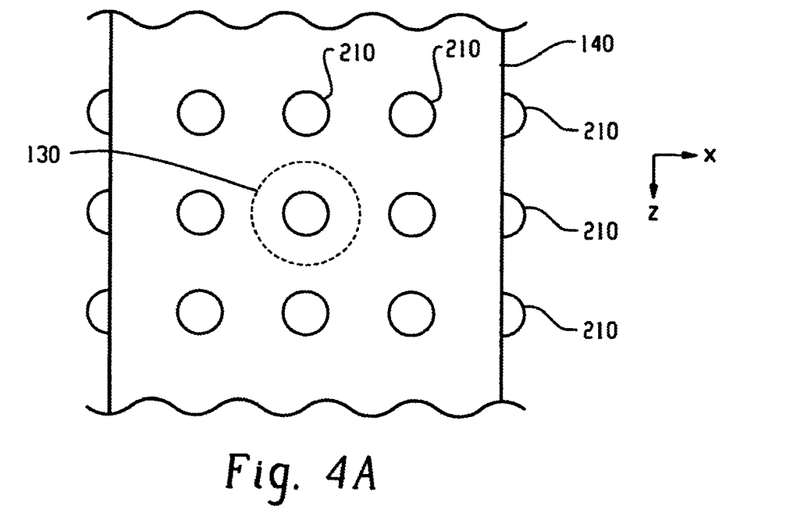
FIG. 4A is a frontal view of a section of a subject with fiducial markers placed thereon.
Figure 4B:
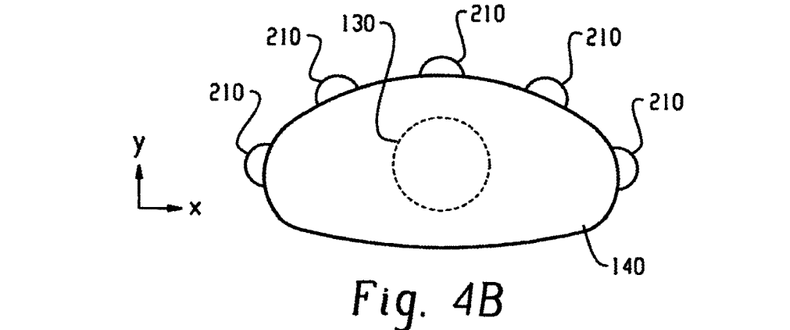
FIG. 4B is an axial view of a section of a subject with fiducial markers placed thereon.
Figure 4C:
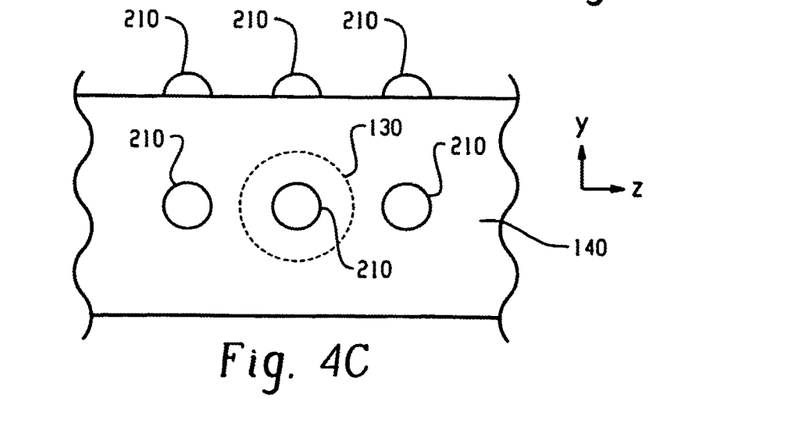
FIG. 4C is a side view of a section of a subject with fiducial markers placed thereon.

In operation, a given number of fiducial markers 210 are placed on the subject as shown in FIGS. 4A-4C. As can be seen, the markers a placed on the subject 140 in the vicinity of the target tissue to be treated 130. In one embodiment, the markers are randomly placed on the subject. In another embodiment, the markers are evenly positioned on the subject. In still another embodiment, the markers are placed on known landmarks of the subject. Also, in the embodiment shown, fifteen markers are placed on the subject, however more or less markers may be used as desired.

Once the markers 210 are positioned, the subject is placed on the subject support 120 of the MRI apparatus 100 and the subject is positioned in the examination region 110. As shown in FIG. 1 and FIGS. 4A-4C, the tumor 130 is in the abdominal region and the markers 210 are placed on the abdominal and thoracic regions. It is to be appreciated, however, that the positions of the tumor and markers are not limited to these regions.

An MRI examination is then carried out on the subject. In one embodiment, a cine study is performed using the MRI apparatus and applying known imaging techniques to image the target tissue 130. Concurrently, the reference marker localizer 160 collects data with respect to the reference markers 210. Here the target tissue 130 and the reference markers 210 can be imaged during dynamic activity, such as subject breathing or other movement that would cause a predictable movement of the tumor with respect to the fiducial markers. The examination is performed for a duration of, for example three minutes, during which time, the subject breathes normally. It is to be understood that the duration of the examination can be more or less than three minutes depending on the amount of cine image data that is desired. It is also to be understood that rather than breathing normally, the subject may breathe in an alternate prescribed manner.

After this preparatory scan is completed, the image data are displayed statically on the MRI localizer. Here, the tumor position is identified using known oncological procedures, such as contouring. Contouring is performed by the operator using the pointing device 152 to draw contours, or place other marks, around the tumor in a given number of images displayed on the display 151. From the tumor identification data, a tumor isocenter can then be identified in the MR images.

In addition to the tumor, the fiducial markers are also identified and uniquely labeled. The markers are optionally identified by the user or automatically as is known in the art, via the reference marker localizer 160.

In an alternate embodiment, the reference markers 210 appear on the MR cine images and are displayed on the MRI localizer. Here, the reference markers are localized by the operator using the pointing device 152 to mark the fiducials as they appear on the display 151.

Once the tumor and the fiducial markers have been localized as described above, the localization data are passed to the tracking processor 300. In one embodiment, the tracking processor calculates distances, for example $\Delta x$, $\Delta y$, and $\Delta z$, between the tumor isocenter and individual fiducial markers. The tracking processor then performs a correlation between the distances and the markers. A look-up table is then generated such that for a given position of a fiducial marker, or markers, the position of the tumor isocenter can be found.

In another embodiment, tumor position is generated as a function of fiducial marker position for the individual markers. The function may be a linear function. It may also be non-linear and may include cross-terms (e.g. motion of the tumor in the x-direction may be a function of, inter alia, motion of a given fiducial in the y-direction).

In one embodiment, the tracking processor identifies three fiducials which most accurately predict the tumor position with respect to the fiducials. In other words, a first fiducial is identified for tracking tumor motion in the x-direction, a second fiducial is identified for tracking tumor motion in the y-direction, and a third fiducial is identified for tracking tumor motion in the z-direction. In this way, three external fiducials can be used to predict the position of the tumor.

Those skilled in the art will recognize that better tracking may be realized by using several fiducials per axis to gain better predictive tumor position results. Also, by performing the MRI cine study for several minutes, a statistical degree of confidence can be built up which confirms that there is a good correlation between tumor isocenter and the external fiducials. Regardless of the parameters of the cine study and tracking/modeling method, the tracking processor produces a mathematical tracking model which describes the relationship between the fiducial positions and the tumor position. The model parameters are then sent to the treatment controller 460 and the treatment protocol is carried out as described more fully below.

Once the parameters of the tracking model have been determined, and optionally the markers to be used to predict the position of the tumor have been selected, the other fiducials can be removed as desired. The subject is then placed in position B such that the location of the fiducials can be monitored and the tumor can be treated by the interventional tool 400.

For the embodiment shown in FIG. 1, during a radiation treatment session, the positions of the fiducials are monitored in real time by the reference marker localizer 160. Once the fiducials have been localized, the related position information is passed to the treatment controller 460. The treatment controller then uses the fiducial positions as input to the tracking model generated by the tracking processor 300 to predict the position of the tumor during treatment.

Typically, an oncology linac x-ray system such as that shown in FIG. 1 includes three inputs: gantry, table, and collimator. The gantry input specifies an angular orientation of the C-arm 420 around the subject and a canting of the plane of the C-arm relative to a longitudinal axis of the subject. The table of an oncology linac system can typically move in three directions, up-down, longitudinally back and forth, and canting relative to a longitudinal axis of the subject. Finally, the collimator input adjusts the angle of a collimator 411 and a size of an aperture of the linac 410. This makes the beam of x-rays wide or narrow, depending on the desired path and diameter.

Accordingly, as the fiducials move, the treatment controller uses the fiducial position information to control the inputs to the treatment tool 400 so that the treatment can be directed at the target more accurately than if the treatment tool were not so controlled.

In another embodiment, a model is developed which predicts rotations of the tumor separately or in conjunction with the motion of tumor isocenter. As with the motion model described above, the external fiducial markers are used to make such prediction. The treatment tool is then controlled as described above, taking into account such rotation.

In another embodiment, a model is developed which predicts distortions of the tumor separately or in conjunction with rotation and motion. As with the motion model, the external fiducial markers are used to make such prediction. The treatment tool is then controlled as described above, taking into account such distortion.

In another embodiment, the MR cine study is performed prior to each radiation treatment session so that tumor shrinkage, body mass and/or shape changes can be accounted for.

Figure 5:
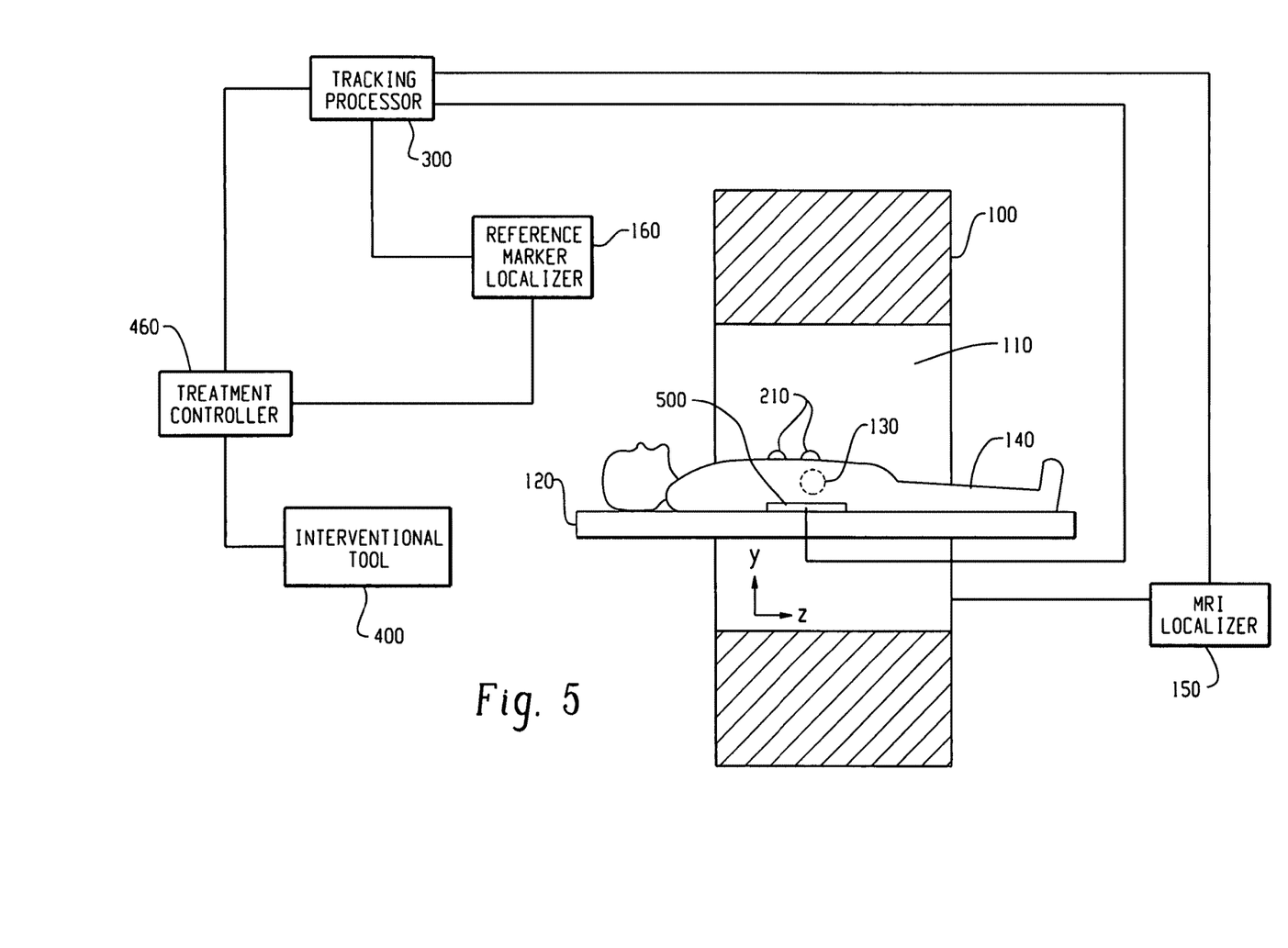
FIG. 5 is an illustration of a target treating apparatus which utilizes fiducial markers and a pressure transducer.

In yet another embodiment, external transducers other than the fiducial markers are used to facilitate the accuracy of the tumor position model described above. For example, as shown in FIG. 5, a pressure sensor 500 is placed under the subject. The pressure data are synchronized with the MRI data for the tumor and the fiducial markers and changes in weight distribution throughout the breathing cycle is used as input into the tracking processor. The tracking processor then uses the pressure data, along with the fiducial marker data to create the model of target motion. Other types of external transducers that are contemplated include traditional gating bellows, breathing sensors attached to the nose/mouth, ECG signals, and Vector ECG signals.

Figure 6:
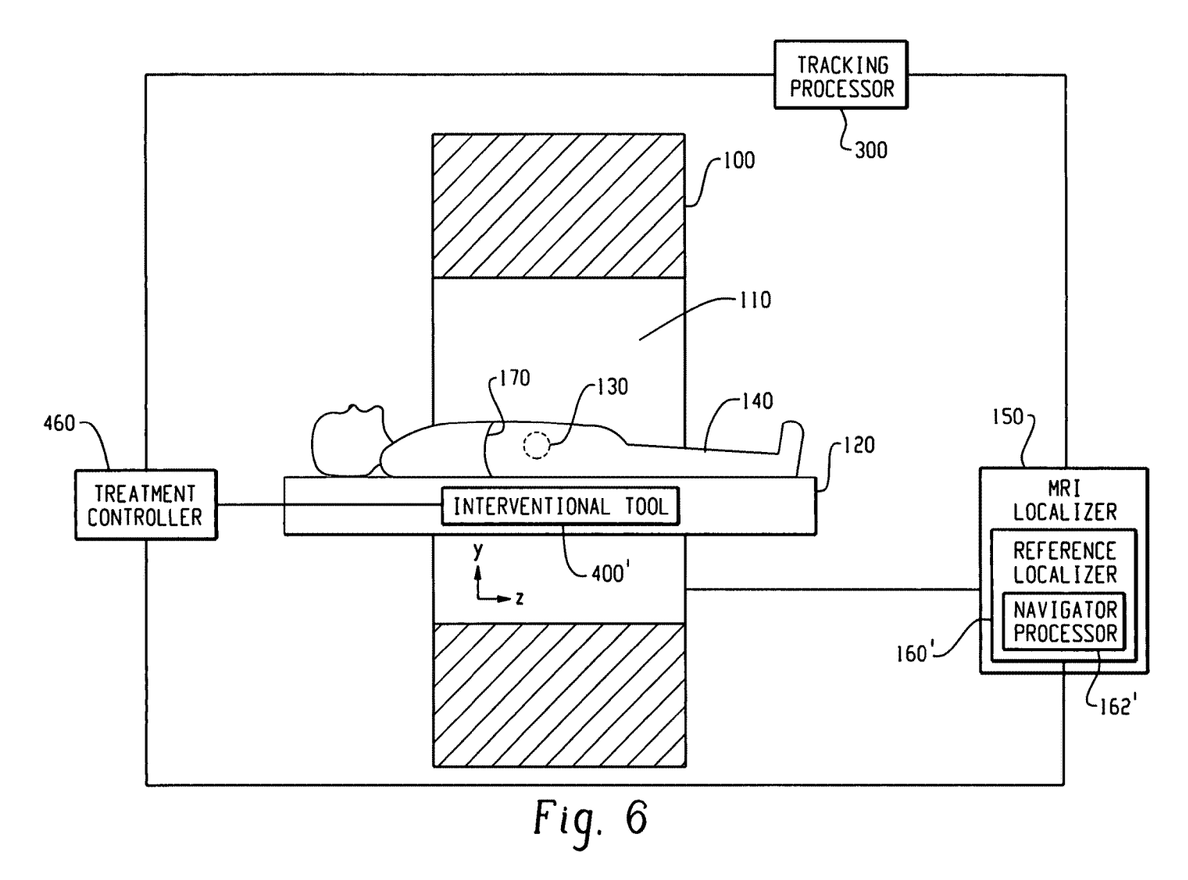
FIG. 6 is an illustration of a target treating apparatus which utilizes navigators for target tracking.

In yet another embodiment, as shown in FIG. 6, rather than using external markers as described above, the position of the region of interest 130 can be predicted non-invasively using MR navigators. As can also be seen in FIG. 6 an interventional tool 400' is located within the examination region 110 of the MRI apparatus 100 and in proximity to the target 130. Here, the interventional tool can be a focused ultrasound device situated under the subject 140 and in the subject support 120. More specifically, the ultrasound device can be a phased-array transducer where multiple focal points can be treated simultaneously and/or transducers can be controlled to follow the motion of a target as described herein. Alternately, a focal point of an ultrasound device can be moved to follow a target.

In one embodiment, the MR scanner is a 1.5T system equipped with an MR compatible 14-ring spherical ultrasound transducer integrated in the bed of the MR system. The ultrasound transducer includes an operating frequency of 1.5 MHz, an aperture diameter of 96 mm, a radius curvature of 130 mm, and a maximum acoustic power of 44 W averaged over the electric duty cycle. The ultrasound probe can be hydraulically moved in a horizontal plane with a spatial resolution of 0.25 mm in each direction, covering an 80×80 mm square. The focal length associated with this embodiment can be adjusted from 80 to 150 mm. It is to be understood that other operating parameters for the MRI system and ultrasound device are contemplated and can be selected as necessary.

Figure 7:
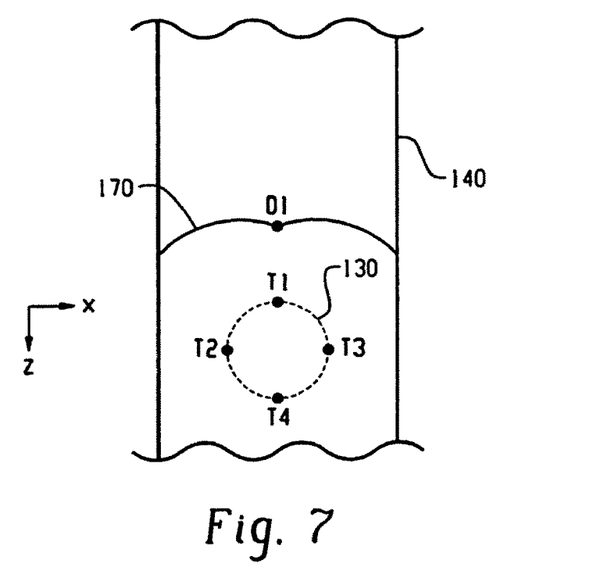
FIG. 7 is a frontal view of a section of a subject showing localized points for target tracking.

In a preparation phase, the MRI apparatus 100 generates images of the subject which include the subject's diaphragm 170 and the target tissue 130. Various points, or contours, on the diaphragm 170 and target tissue are then identified on the MRI localizer 150. Accordingly, in this embodiment, it is understood that the reference localizer 160' can be integrated into the MRI localizer as shown in FIG. 6. As shown in FIG. 7, point D1 is identified on the diaphragm and points T1, T2, T3, and T4 are identified on the target tissue. It is to be understood that more or less points can be identified on the diaphragm and target as desired. It is also to be understood that other structures, such as the chest wall, can be localized separately or in conjunction with the diaphragm.

The localized data are then passed to the tracking processor 300 and a model is generated which relates the position of the target as a function of the position of the diaphragm. The model is then passed to the treatment controller 460.

During subsequent treatment, the position of the diaphragm is monitored using reference marker localizer 160'. This can be performed using navigator scans which automatically detect the position of the diaphragm. More specifically, during treatment, the MRI apparatus generates navigator scan data for the navigator points localized during the preparation phase. These points are automatically identified by the reference marker localizer 160' using a navigator processor. Here, the localizer includes a navigator processor 162'. Accordingly, although it may be desirable, it is not necessary to image the target tissue 130 during the treatment phase.

The treatment controller then, having received the motion model parameters from the tracking processor and the navigator data from the reference marker localizer, controls the interventional device 400 as desired. In the embodiment shown, a focused ultrasound ablator 400' is controlled to treat the tumor 130 while it moves during normal subject movement, such as breathing.

The following examples provide additional explanation as to the operation of an embodiment of the invention. In a preparation phase a subject specific motion model is measured. For this purpose a time series of images (e.g. low resolution images) is measured during free respiration. Selected points of the diaphragm or other reference anatomical structures (e.g chest wall, or other abdominal or thoracic structures) are measured using navigators and stored in a vector S(t). In a simple version, the navigators are one-dimensional MR sub-experiments. The vector S(t) contains the position of the corresponding structures as a function of time.

The MR images are then be registered according to a chosen motion model. For example, the model may be a 3D rigid body motion model or an affine transform which takes into account translation, rotation, scaling, and shear parameters. The corresponding model parameters are stored in a matrix A, which reflects the temporal changes of the corresponding parameters.

Using an appropriate mathematical transform, for example principal component analysis, a matrix B is determined which maps the navigator data S(t) onto a model parameter A'(t) in the sense of a statistical average where A'(t)=B*S(t). This model provides for deriving the actual motion state of the target region as a function of time based on the navigator data.

By way of a more specific example, in a short free-breathing calibration scan, a time series of low-resolution "single-shot" 3D datasets are acquired depicting the respiratory motion of the target tissue. A motion registration algorithm at the localizer 150 determines a set of model parameters for each 3D dataset reflecting the current respiratory motion state of the target. Subsequently, the tracking processor performs a statistical data analysis, for example based on a principal component analysis (PCA), to find the correspondence between the model parameters and the navigators. Consequently, at any time during the successional high-resolution coronary MRA scan an estimated motion state can be predicted from the currently measured navigator displacements, which is then used for prospective motion correction during the immediately following data acquisition step.

The motion considered can be described by a time-variant linear transformation A(t) and an additional translation d(t), which transforms each initial spatial point position $r=[x, y, z]^T$ to a new position R(r, t)

$$rR(r,t) = A(t)r + d(t) \quad (1)$$

with and $$A(t) = \begin{bmatrix} 1+a_{xx} & a_{xy} & a_{xz} \\ a_{yx} & 1+a_{yy} & a_{yz} \\ a_{zx} & a_{zy} & 1+a_{zz} \end{bmatrix} \quad (2)$$

$$d(t) = \begin{bmatrix} d_x \\ d_y \\ d_z \end{bmatrix}$$

The matrix A(t) represents a general 3D linear transformation, which can be interpreted as the combination of rotations, scale, and shear transformations. The combination of the linear transformation and a translation is an affine transformation. The entries of matrix A and vector d are given as a function of the employed navigators, which are represented by a vector s(t) containing the current displacements obtained by the navigators. The relation between the model parameters and the navigators can be adapted to the individual movement (e.g. breathing) pattern, which is described below.

For the preparatory scan, a multislice 2D fast gradient echo sequence (TFE-EPI) can used to acquire a series of low-resolution 3D datasets depicting the respiration-induced motion of the target over several respiratory cycles.

Three pencil-beam navigators can be applied prior to the imaging block to characterize the current motion state. The navigators can be placed on the dome of the diaphragm in SI, on the anterior chest wall in AP, and on the right margin of the chest cavity in RL orientation. But, in principle, other navigator configurations may be possible, as long as the monitored tissue structure correlates well with the respiration-induced motion of the target.

After the scan, the 3D datasets are used to register 3D translational or 3D affine motion of the target with respect to an automatically selected reference dataset representing, for example, end-expiration. A manually defined 3D mask can be used to roughly suppress signal originating from tissue surrounding the target which may otherwise affect the accuracy of the motion registration of the target. A model-based registration algorithm on the basis of a global cross correlation measure and a Gauss-Newton optimization is used for motion registration. The output of the registration procedure is a series of parameter vectors a(t), each representing the detected m model parameters of one single 3D dataset acquired at time t. In case of the 3D translation model the model parameter vector $a(t)=[d_x, d_y, d_z]^T$ contains three translation components (m=3) and in case of the affine transformation $a(t)=[a_{xx} \ldots a_{zz}, d_x, d_y, d_z]^T$ contains nine parameters $a_{ij}$ of the linear transformation and additional three translation components $d_i$ (m=12 parameters in total).

The relation between the m model parameters combined in a(t) and the n navigator signals $s(t)=[s_{SI}, s_{AP}, s_{RL}, \ldots]^T$ is then found which is represented by the time-invariant coefficient matrix B:

$$a(t)=B\,s(t).$$

Thus, each model parameter is expressed as a linear combination of the current n navigator signals. The coefficient matrix B can be determined from the registration results a(t) and the measured navigator displacements s(t) by means of a statistical multivariate analysis similar to a multiple regression method. One potential problem can be potential multicollinearities, which occur if there are near-constant linear functions of two or more of the variables resulting in unstable or misleading solutions. Accordingly, in one embodiment, a principal component analysis (PCA) is used for data analysis.

The PCA is a statistical multivariate method commonly used to reduce the dimensionality of a given set of variables by transforming the original variables, which are the model parameters and the navigator signals here, to a set of new variables, namely, the principal components (PCs). The PCs are linear-independent and orthogonal in parameter space. Only a few of the strongest PCs suffice to cover the vast majority of system variability. The relation between model parameters and navigators is derived from these few strongest PCs.

The procedure for the data analysis is as follows: The model parameters a(t) and the navigators s(t) are combined to a new vector of M=n+m variables $p(t)=[a_{xx} \ldots a_{zz}, d_x, d_y, d_z, s_{SI}, s_{AP}, s_{RL}, \ldots]^T$. The centered variable vectors $$\tilde{p}(t)=p(t)-\bar{p}$$

with the mean parameter vector $$\bar{p} = \frac{1}{N}\sum_{k=1}^{N} p(t_k)$$

representing the mean motion state and the number of sample points N (cardiac cycles covered by the calibration scan). The covariances between the elements of the centered variable vectors are given by the empirical covariance matrix $$C=\tilde{P}\tilde{P}^T$$

where the matrix $$\tilde{P}=[\tilde{p}(t_1), \tilde{p}(t_2) \ldots \tilde{p}(t_N)]$$

contains the centered vectors of variables $$\tilde{p}(t)$$

at all sample time points t of the complete calibration scan. Next, the eigenvalues $\lambda_1, \lambda_2, \ldots \lambda_M$ and the corresponding eigenvectors $q_1, q_1, \ldots q_M$ of the covariance matrix C are calculated, which are the PCs or the major modes of variation of the system. An approximation of each possible motion state can be expressed as a weighted sum of the first µ eigenvectors $$p'=\bar{p}+Qw$$

with matrix $Q=[q_1, q_1, \ldots q_\mu]$ consisting of the first µ eigenvectors. w is a vector of weight factors, representing a new set of variables in the coordinate system of the PCs, which is of minor importance in this context and which will be eliminated in the next step. The above equation for p' means a reduction of the system dimensionality from initially M=15 parameters (12 affine model parameters+3 navigators) to typically µ=3 or less parameters. The number of eigenvectors or PCs is determined during the phase of selecting the optimal combination of navigators described below. The system of equations given for p' can be split into two separate ones $$a'=Q_a\,w$$

$$s'=Q_s\,w$$

with $p'=[a', s']^T$ and where $Q_a$ contains the top m rows and $Q_s$ the bottom n rows of Q with the number of model parameters m and the number of navigators n. The constant average variable vector p can be omitted here, since we are only interested in the variation of the system. The elimination of w yields $$a'=Bs \text{ with } B=Q_a Q_s^{-1}$$

B is the desired coefficient matrix to be used for calculation of the estimated model parameters a'(t) from the current navigator signals s(t) required for motion correction during the subsequent scan. After the calibration procedure, the coefficient matrix B is provided to the treatment controller to be available for the subsequent treatment scan.

After the preparation procedure, the position of the target can be predicted with a neglectable latency (e.g. 10-30 ms) using navigators acquired in real-time. This information can be used to support the intervention either performed manually by the physician using appropriate display or overlays tools or by controlling interventional tools automatically by feeding back the position information to the treatment controller.

Accordingly, using an MR integrated focused ultra-sound (US) array tumor ablation can be performed, for example, in the kidney region. A respiratory motion model for the tumor region is established using an MR imaging protocol, which is correlated to, for example, the right hemi-diaphragm position. During therapy inside the MR-scanner, navigators are applied (on a roughly one second time base) to probe the current respiratory state. Based on the navigator data, the motion state of the tumor region can be derived and predicted in real-time. This information steers the US-ablation array to treat the tumor. The information can also be used to guide robotic arm biopsy procedures, other minimally invasive surgical procedures, and the like.

This concept can be extended using not only one-dimensional navigators but to multi-dimensional navigators as well.

The invention has been described with reference to the preferred embodiment. Obviously, modifications and alterations will occur to others upon reading and understanding the preceding description. It is intended that the invention be construed as including all such modifications and alterations insofar as they come within the scope of the appended claims or the equivalents thereof.

What is claimed is:

1. A targeted treatment apparatus, the apparatus comprising:
    a magnetic resonance imaging apparatus that non-invasively obtains image data and reference data of a subject disposed within an examination region during a pretreatment session;
    a magnetic resonance imaging localizer that receives the image data and localizes a target region to provide a sequence of target locations associated with one or more target points in the target region;
    a reference marker localizer that receives the reference data and provides therefrom a sequence of reference locations of one or more reference points on an internal anatomic structure of the subject, the internal anatomic structure being remote from the target region;
    a tracking processor that receives the sequence of target locations and the sequence of reference locations and creates a tracking model that defines a mapping between the reference locations and the target locations;
    an intervention tool that directs a treatment to the target region; and
    a treatment controller that controls the intervention tool;
    wherein, in a subsequent treatment session:
    the magnetic resonance imaging apparatus provides subsequent reference data;
    the reference marker localizer receives the subsequent reference data and provides therefrom one or more subsequent reference locations of the one or more reference points on the internal anatomic structure, and
    the treatment controller receives the one or more subsequent reference locations and uses the tracking model to determine corresponding subsequent target locations, and uses the subsequent target locations to direct the intervention tool to the target region.

2. A method of treating a target region within a subject, the method comprising:
    generating, non-invasively, magnetic resonance images and reference data of the subject disposed within an examination region during a pretreatment session;
    localizing the target region from the magnetic resonance images to provide a sequence of target locations associated with one or more target points in the target region;
    localizing one or more reference points on an internal anatomic structure in proximity to the target region based on the reference data to provide a sequence of reference locations of the one or more reference points, the internal anatomic structure being remote from the target region; and
    generating a relationship between the reference locations of the one or more reference points and the target locations of the one or more target points based on the sequences of reference locations and target locations;
    generating subsequent reference data during a treatment session;
    localizing one or more subsequent reference points based on the subsequent reference data to provide one or more subsequent reference locations on the internal anatomic structure;
    determining corresponding one or more subsequent target locations based on the subsequent reference locations and the generated relationship between the locations of the one or more reference points and the one or more target points; and
    controlling an intervention tool to direct a treatment to the target region based on the determined one or more subsequent target locations.

3. A non-transitory computer-readable medium that includes a program that causes a processor to:
    generate, non-invasively, magnetic resonance images and reference data of subject disposed within an examination region during a pretreatment session;
    localize target region from the magnetic resonance images to provide a sequence of target locations associated with one or more target points in the target region;
    localize one or more reference points on an internal anatomic structure in proximity to the target region based on the reference data to provide a sequence of reference locations of the one or more reference points, the internal anatomic structure being remote from the target region; and
    generate a relationship between the reference locations of the one or more reference points and the target locations of the one or more target points based on the sequences of reference locations and target locations;

generate subsequent reference data during a treatment session;

localize the one or more reference points based on the subsequent reference data to provide one or more subsequent reference locations on the internal anatomic structure;

determine corresponding one or more subsequent target locations based on the subsequent reference locations and the generated relationship between the locations of the one or more reference points and the one or more target points; and control an intervention tool to direct a treatment to the target region based on the determined one or more subsequent target locations.

4. The medium of claim 3, wherein the anatomic structure is a diaphragm of the subject.

5. The medium of claim 4, wherein the one or more target points include a plurality of target points on the diaphragm.

6. The medium of claim 3, wherein the anatomic structure includes a chest wall of the subject.

7. The medium of claim 3, wherein the non-invasive generation of the reference data includes providing MR navigator signals.

8. The medium of claim 3, wherein the controlling of the intervention tool enables the intervention tool to provide a substantially continuous treatment.

9. The medium of claim 3, wherein determining the one or more subsequent target locations includes predicting the target locations based on motion of the reference points.

10. The apparatus of claim 1, wherein the anatomic structure is a diaphragm of the subject.

11. The apparatus of claim 10, wherein the one or more target points include a plurality of target points on the diaphragm.

12. The apparatus of claim 1, wherein the anatomic structure includes a chest wall of the subject.

13. The apparatus of claim 1, wherein the magnetic resonance imaging apparatus non-invasively obtains the reference data through a use of MR navigator signals.

14. The apparatus of claim 1, wherein the treatment controller controls the intervention tool to provide a substantially continuous treatment.

* * * * *